(12) United States Patent
Aklian

(10) Patent No.: US 7,349,080 B2
(45) Date of Patent: Mar. 25, 2008

(54) LABEL-INDEPENDENT DETECTION OF UNPURIFIED ANALYTES

(75) Inventor: Mannix V. Aklian, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 150 days.

(21) Appl. No.: 11/026,387

(22) Filed: Dec. 30, 2004

(65) Prior Publication Data

US 2006/0146317 A1 Jul. 6, 2006

(51) Int. Cl.
*G01N 21/41* (2006.01)

(52) U.S. Cl. .................................................... 356/128

(58) Field of Classification Search ................. 356/128, 356/130, 132, 136
See application file for complete search history.

(56) References Cited

U.S. PATENT DOCUMENTS

| | | | | |
|---|---|---|---|---|
| 4,815,843 | A | 3/1989 | Tiefenthaler et al. | 356/128 |
| 4,889,427 | A | 12/1989 | Van Veen et al. | 356/445 |
| 5,991,488 | A | 11/1999 | Salamon et al. | 385/129 |
| 6,542,229 | B1 * | 4/2003 | Kalal et al. | 356/128 |
| 6,617,116 | B2 | 9/2003 | Guan et al. | 435/7.1 |
| 6,728,429 | B1 | 4/2004 | Melman et al. | 385/12 |
| 6,771,376 | B2 | 8/2004 | Budach et al. | 356/521 |
| 6,818,886 | B2 | 11/2004 | Tiefenthaler | 250/282 |
| 6,899,849 | B2 * | 5/2005 | Meinhart et al. | 422/82.09 |
| 2002/0127565 | A1 | 9/2002 | Cunningham et al. | 435/6 |
| 2002/0137055 | A1 | 9/2002 | Erb et al. | 435/6 |
| 2002/0160534 | A1 | 10/2002 | Herron et al. | 436/518 |
| 2002/0168295 | A1 | 11/2002 | Cunningham et al. | 422/82.05 |
| 2003/0008325 | A1 | 1/2003 | Chiulli | 435/7.1 |
| 2003/0017580 | A1 | 1/2003 | Cunningham et al. | 435/287.2 |
| 2003/0017581 | A1 | 1/2003 | Li et al. | 435/287.2 |
| 2003/0026891 | A1 | 2/2003 | Qiu et al. | 427/58 |
| 2003/0027327 | A1 | 2/2003 | Cunningham et al. | 435/287.2 |
| 2003/0027328 | A1 | 2/2003 | Cunningham et al. | 435/287.2 |
| 2003/0032039 | A1 | 2/2003 | Cunningham et al. | 435/6 |

(Continued)

FOREIGN PATENT DOCUMENTS

EP 0 472 990 6/1995

(Continued)

OTHER PUBLICATIONS

Andreas P. Abel et al., "Fiber-Optic Evanescent Wave Biosensor for the Detection of Oligonucleotides", Anal. Chem., 1996, vol. 68, pp. 2905-2912.

(Continued)

*Primary Examiner*—Roy M Punnoose
(74) *Attorney, Agent, or Firm*—Thomas R. Beall; John L. Haack

(57) ABSTRACT

The present invention features use of evanescent field sensing to detect or evaluate unpurified, unlabeled analytes in raw samples. Capture molecules capable of binding to an analyte of interest can be immobilized to a sensing surface of an evanescent field sensor. The interaction between the analyte of interest in a raw sample and the immobilized capture molecules alters the refractive index at the sensing surface, thereby producing a detectable signal in the reflected light from the surface. Raw samples amenable to the present invention include, but are not limited to, cell lysates, tissue extracts, bodily fluid, or biologically-derived samples. Evanescent field sensors suitable for the present invention include, but are not limited to, grating-coupled waveguides.

18 Claims, 3 Drawing Sheets

Lysate with SA Corrected

U.S. PATENT DOCUMENTS

| | | | |
|---|---|---|---|
| 2003/0059855 A1 | 3/2003 | Cunningham et al. | 435/7.9 |
| 2003/0068657 A1 | 4/2003 | Lin et al. | 435/7.9 |
| 2003/0077660 A1 | 4/2003 | Pien et al. | 435/7.1 |
| 2003/0092075 A1 | 5/2003 | Pepper | 435/7.9 |
| 2003/0113766 A1 | 6/2003 | Pepper et al. | 435/6 |
| 2004/0132172 A1 | 7/2004 | Cunningham et al. | 435/287.2 |
| 2004/0132214 A1 | 7/2004 | Lin et al. | 436/518 |
| 2004/0151626 A1 | 8/2004 | Cunningham et al. | 422/58 |
| 2004/0191765 A1* | 9/2004 | Mozdy et al. | 435/5 |
| 2004/0223881 A1 | 11/2004 | Cunningham et al. | 422/82.05 |

FOREIGN PATENT DOCUMENTS

| | | |
|---|---|---|
| WO | WO 91/16425 | 10/1991 |
| WO | WO 98/27430 | 6/1998 |
| WO | WO 02/35214 | 5/2002 |
| WO | WO 2005/012886 | 2/2005 |
| WO | WO 2005/033680 | 4/2005 |

OTHER PUBLICATIONS

Yan Kong et al., "Label-Free Detection in High-Throughput Format for Cytokine Binding Interaction and Functional Kinase Assays", Johnson & Johnson Pharmaceutical Research & Development, L.L.C. and Corning Incorporated.

* cited by examiner

FIG. 1

LID TEST PLATE

|   | 1 | 2 | 3 | 4 | 5 | 6 | 7 | 8 | 9 | 10 | 11 | 12 |
|---|---|---|---|---|---|---|---|---|---|----|----|----|
| A |   |   |   |   |   |   |   |   |   |    |    |    |
| B |   |   | BIOTIN | BIOTIN | BIOTIN | BIOTIN |   |   |   |    |    |    |
| C |   |   | BIOTIN | BIOTIN | BIOTIN | BIOTIN |   |   |   |    |    |    |
| D |   |   | BIOTIN | BIOTIN | BIOTIN | BIOTIN |   |   |   |    |    |    |
| E |   |   | BIOTIN | BIOTIN | BIOTIN | BIOTIN |   |   |   |    |    |    |
| F |   |   | DEX | DEX | DEX | DEX |   |   |   |    |    |    |
| G |   |   | DEX | DEX | DEX | DEX |   |   |   |    |    |    |
| H |   |   | EA | EA | EA | EA |   |   |   |    |    |    |

SOURCE

|   | 1 | 2 | 3 | 4 | 5 | 6 | 7 | 8 | 9 | 10 | 11 | 12 |
|---|---|---|---|---|---|---|---|---|---|----|----|----|
| A | PBS | PBS |   |   |   |   | STR+lys | STR+lys |   | EA | EA |    |
| B | PBS | PBS |   |   |   |   | STR+lys | STR+lys |   | EA | EA |    |
| C | PBS | PBS |   |   |   |   | lys | lys |   | EA | EA |    |
| D | PBS | PBS |   |   |   |   | lys | lys |   | EA | EA |    |
| E | PBS | PBS |   |   |   |   | STR | STR |   | EA | EA |    |
| F | PBS | PBS |   |   |   |   | STR+lys | STR+lys |   | EA | EA |    |
| G | PBS | PBS |   |   |   |   | lys | lys |   | EA | EA |    |
| H | PBS | PBS |   |   |   |   | STR | STR |   | EA | EA |    |

Lysate with SA Corrected

LABEL-INDEPENDENT DETECTION OF UNPURIFIED ANALYTES

FIELD OF THE INVENTION

The present invention relates to methods of using evanescent field sensing to detect or evaluate unlabeled, unpurified analytes of interest.

BACKGROUND OF THE INVENTION

The study of molecular interactions in the high-throughput screening environment is of critical importance to the drug discovery and development process. Many of these screening methods require purification of the molecules to be studied. This process, however, is time consuming and labor intensive. In addition, once the molecules are isolated, labels are often required in order to monitor the interactions between different molecules. This labeling process may also be expensive or time consuming. Therefore, there is a need for new screening methods that require neither purification nor detectable labels.

SUMMARY OF THE INVENTION

The present invention features the use of evanescent field sensing techniques for detection or evaluation of unpurified, unlabeled analytes of interest. Capture molecules capable of binding to the analytes of interest can be immobilized to a sensing surface of an evanescent field sensor. Binding of the unpurified, unlabeled analytes to the capture molecules alters the refractive index at the sensing surface, thereby producing a detectable signal in the reflected light from the surface.

In one aspect, the present invention provides methods of using evanescent field sensing for evaluating or monitoring interactions between an unpurified analyte and a capture molecule. These methods comprise the steps of:

contacting a raw sample with a sensing surface of an evanescent field sensor, where the raw sample comprises the analyte, and the sensing surface is coated with the capture molecule; and detecting a change in the refractive index at the sensing surface. The change in the refractive index indicates whether the analyte is capable of interacting with the capture molecule.

In many embodiments, the evanescent field sensors employed in the present invention are grating-coupled waveguides, such as those described in U.S. Pat. No. 4,815,843 or U.S. Pat. No. 6,985,664, entitled "Substrate Index Modification for Increasing the Sensitivity of Grating-Coupled Waveguides". The operation of a grating-coupled waveguide typically involves:

directing a light beam (e.g., a laser beam) into the waveguide to produce an evanescent tail that extends beyond a sensing surface coated with capture molecules; and receiving a reflected light beam from the waveguide to detect a resonant condition that indicates whether an analyte in the sample binds to the immobilized capture molecules.

Raw samples amenable to the present invention include, but are not limited to, cell lysates, supernatants of cultured cells, bodily fluids, tissue extracts, food or beverage samples, pharmaceutical samples, clinical samples, or other samples that have not been subject to substantial purification. In one example, the raw sample being analyzed is a lysate or supernatant of cultured cells, and the analyte of interest is a recombinant protein expressed by the cultured cells.

In many cases, control samples are used to determine baseline refractive index changes at the sensing surface. The desired signals, such as refractive index changes caused by the binding of an analyte of interest to the sensing surface, can be extracted by comparing the refractive index changes produced by the raw sample of interest to the baseline refractive index changes. Preferably, a control samples is prepared from the same source as the raw sample being analyzed, but does not include the analyte of interest. Other types of control samples, such as blocking buffers containing bovine serum albumin or other proteins, can also be used.

In another aspect, the present invention features methods for evaluating or monitoring molecular interactions in multi-sample formats. These methods comprise the steps of:

contacting a plurality of raw samples with respective sensing surfaces of an evanescent field sensor, where each raw sample comprises an analyte of interest, and each sensing surface is coated with a capture molecule; and detecting a change in the refractive index at each sensing surface. The change in the refractive index at each sensing surface indicates whether the captures molecules immobilized at that surface interact with the analyte of interest in the corresponding raw sample.

In one embodiment, the evanescent field sensor comprises a microplate which includes a plurality of wells. Each well comprises or incorporates a grating-coupled waveguide that includes a sensing surface coated with capture molecules.

The present invention also features methods for detecting the presence or absence of an analyte of interest in raw samples. These methods comprise the steps:

contacting a raw sample with a sensing surface of an evanescent field sensor, where the sensing surface is coated with capture molecules capable of binding to the analyte of interest; and detecting a change in the refractive index at the sensing surface. The change in the refractive index is indicative of the presence or absence of the analyte of interest in the raw sample.

In one embodiment, the raw sample is a bodily fluid sample (e.g., blood, serum, sputum, tears, sweat, semen or urine) or a tissue extract (e.g., a brain or lung extract), and the analyte of interest is an antibody specific to an epitope of a pathogen (such as a virus or bacterium). The immobilized capture molecules comprise the epitope of the pathogen and, therefore, are recognizable by the analyte of interest. In another embodiment, the analyte of interest is a cancer cell marker, and the immobilized capture molecules are antibodies specific to the cancer cell marker.

Other features, objects, and advantages of the invention are apparent in the detailed description that follows. It should be understood, however, that the detailed description, while indicating preferred embodiments of the invention, is given by way of illustration only, not limitation. Various changes and modifications within the scope of the invention will become apparent to those skilled in the art from the detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The drawings are provided for illustration, not limitation.

FIG. 1 diagrammatically illustrates the layout of a source plate and a label-independent detection (LID) test plate employed in the present invention.

DETAILED DESCRIPTION OF THE INVENTION

Figure 2:
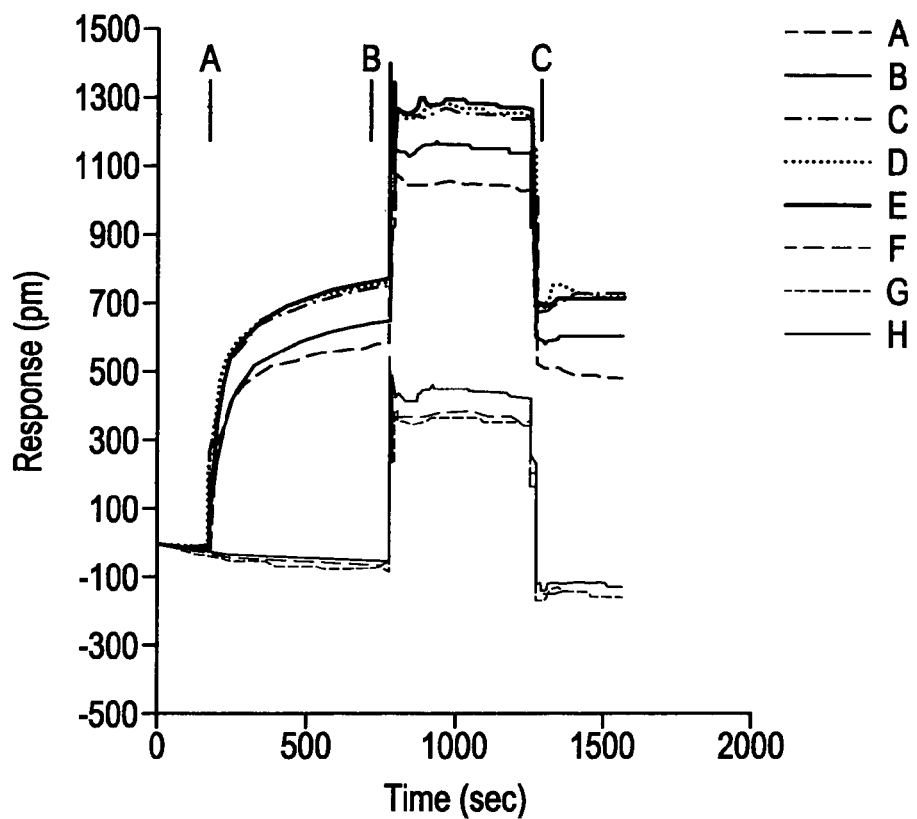
FIG. 2 shows LID interrogation of interactions between purified streptavidin and immobilized biotin.

The present invention features the use of evanescent field sensing for detecting or evaluating unpurified, unlabeled analytes in raw samples. Capture molecules capable of binding to an analyte of interest can be immobilized at a sensing surface of an evanescent field sensor. The interaction between the analyte of interest in a raw sample and the immobilized capture molecules alters the refractive index at the sensing surface, which in turn produces a detectable signal in the reflected light from the surface. Raw samples amenable to the present invention include, but are not limited to, cell lysates, tissue extracts, bodily fluid, or other biologically-derived samples. Microbial samples, food/beverage samples, or other crude samples that have not been subject to substantial purification can also be analyzed according to the present invention. The ability to detect unlabeled analytes in raw samples by evanescent field sensing is unexpected due to the sensitivity of an evanescent field sensing surface to non-specific bindings. Therefore, the present invention represents a significant advance in the field of label-independent detection.

Evanescent field sensing enables label-independent optical monitoring of biological events. When light is channeled along a surface or trapped in a thin layer, the associated electromagnetic field penetrates a small distance (typically about 100-1,000 nm) away from the surface to create a so-called evanescent electromagnetic field. This field can interact with molecules attached to the surface. The interaction of the evanescent electromagnetic field with the surface-attached molecules can be used to detect refractive index changes on the surface which occur when analytes in a sample bind to the molecules immobilized to the surface.

In many embodiments, the evanescent field sensors employed in the present invention are grating-coupled waveguides. Non-limiting examples of grating-coupled waveguides include those described in U.S. Pat. No. 4,815,843 and U.S. Pat. No. 6,985,664, entitled "Substrate Index Modification for Increasing the Sensitivity of Grating-Coupled Waveguides", both of which are incorporated herein by reference in their entireties. A grating-coupled waveguide typically includes a substrate, a diffraction grating, and a waveguide film. The diffraction grating can be directly fabricated into the waveguide film or the substrate. The diffraction grating can also be located in optical proximity to the waveguide film, or even constitutes the waveguide film itself. A light beam (e.g., a coherent laser beam) can be directed into the waveguide from a bottom surface of the substrate and interacts with the diffraction grating and the waveguide film to create an evanescent tail that extends into a sensor region above the waveguide film. Light reflected from the waveguide is received and analyzed to detect resonant conditions that are indicative of the presence or absence of an analyte of interest in the sensing region above the waveguide film.

In one embodiment, the grating-coupled waveguides described in U.S. Pat. No. 6,985,664, entitled "Substrate Index Modification for Increasing the Sensitivity of Grating-Coupled Waveguides" are used for the detection of unlabeled analytes in raw samples. These grating-coupled waveguide include a substrate with an index of refraction of no greater than 1.5 and a waveguide film having a higher index of refraction than the substrate. The low-index substrate effectively increases the field strength of the evanescent tail extending from the sensing surface and therefore significantly improves the detection sensitivity of the waveguide. Suitable materials for making low-index substrates include, but are not limited to, thermoplastic materials, such as polyvinylidene fluoride, polymethylpentene, blends of polyvinylidene fluoride/polymethylmethacrylate, or fluoropolymers (e.g., fluoroacrylate).

Materials having a refractive index of greater than 1.5 can also be used to prepare the substrate of a grating-coupled waveguide employed in the present invention. In addition, glass, $SiO_2$, quartz, polycarbonate (PC), poly(methyl methacrylate) (PMMA), polyimide (PI), polystyrene (PS), polyethylene (PE), polyethylene terephthalate (PET), polyurethane (PU), or other materials can be used to prepare the substrate of a grating-coupled waveguide.

In another embodiment, an array of grating-coupled waveguides (such as in a multi-cell format) is used to detect unlabeled analytes in raw samples. Many methods are available for making grating-coupled waveguides in a multi-well format. See, for example, U.S. Patent No. 6,985,664, entitled "Substrate Index Modification for Increasing the Sensitivity of Grating-Coupled Waveguides". In one example, a grating-coupled waveguide is incorporated into a well of a microplate by first preparing diffraction grates in a low-index ultraviolet-curable material and then transferring the low-index material into the well, followed by exposing the well to ultraviolet light to form a low-index substrate. The low-index substrate can be subsequently coated with a waveguide film.

Other evanescent field sensing systems, such as surface plasmon resonance or resonating mirrors, can also be used for the detection of unlabeled analytes in raw samples. Surface plasmon resonance (SPR) is based on the resonant transfer of electromagnetic energy from the evanescent field of a light beam into electron-photon coupled oscillation in certain metals. A widely deployed SPR technique uses a prism to generate total internal reflection at one of its surfaces. This surface is coated with a thin metallic film, which supports the surface plasmon wave (SPW), whose propagation velocity strongly depends on the index of refraction of the medium in close proximity to the metal surface. See, for example, U.S. Pat. Nos. 5,991,488 and 4,889,427. The change in the index of refraction at the surface alters the angle at which the resonance occurs. The surface can be pre-coated with an immobilized layer of capture molecules that have strong affinities for the analyte of interest. These capture molecules cause the analyte of interest to bind to the surface, thereby modifying the index of refraction at the surface and producing a detectable shift in the SPR curve or the output light intensity.

The present invention contemplates detection or evaluation of any type of analytes, such as proteins, lipids, polysaccharides, nucleic acids, or other chemical compounds of interest. Specific examples of analytes that are amenable to the present invention include, but are not limited to, antigens (such as bacterial or viral antigens), antibodies (such as those induced in response to infection or allergic reactions), cancer markers, growth factors, kinases, phosphatases, proteases, metabolic enzymes, enzyme cofactors, G protein coupled receptors, phospholipases, hormone receptors, G-protein regulators, growth factor receptors, cytokines, trophic factors, signaling effectors, neurotransmitters, ion channels, steroids, hormones, cholesterols, lipoproteins, peptide inhibitors, peptide mimics, therapeutic compounds, illicit drugs, toxins, chelating reagents, mRNA, cDNA, cRNA, genomic sequence fragments, oligonucleotides, expressed sequence tags, cell fragments, cellular substructures, synapses, cell organelles, cancer cells, tissue samples, viruses, bacteria, protozoans, or other infectious or pathogenic agents. The molecule weight of an analyte of interest can be in any range. In many instances, the analytes being detected have a molecular weight of at least 10 kDa, 20 kDa, 30 kDa, 40 kDa, 50 kDa, 60 kDa, 70 kDa, 80 kDa, 90 kDa, 100 kDa, or more. Analytes having a molecular weight of less than 10 kDa can also be evaluated according to the present invention.

In one embodiment, an analyte of interest is a viral or bacterial antigen, or an antibody thereto. Non-limiting examples of viral antigens include those derived from human immunodeficiency viruses (e.g., HIV-1 and HIV-2), influenza viruses (e.g., influenza A, B and C viruses), coronaviruses (e.g., human respiratory coronavirus), hepatitis viruses (e.g., hepatitis viruses A to G), or herpesviruses (e.g., HSV 1-9). Non-limiting examples of bacterial antigens include those derived from *Bacillus* (e.g., *Bacillus anthracis* or *Bacillus cereus*), *Escherichia* (e.g., *Escherichia coli*), *Haemophilus* (e.g., *Haemophilus influenza* or *Haemophilus parainfluenzae*), *Listeria* (e.g., *Listeria monocytogenes*), *Neisseria* (e.g., *Neisseria gonorrhoeae* or *Neisseria meninigitidis*), *Nocardia* (e.g., *Nocardia asteroides*), *Salmonella* (e.g., *Salmonella typhi* or *Salmonella typhimurium*), *Staphylococcus* (e.g., *Staphylococcus aureus*, *Staphylococcus saprophyticus* or *Staphylococcus epidermis*), or *Streptococcus* (e.g., *Streptococcus pyogenes* or *Streptococcus pneumonia*). A viral or bacterial antigen can be, for example, a protein, a lipid, a polysaccharide, or a nucleic acid.

In another embodiment, an analyte of interest is a cancer marker. Many genes are over-expressed in cancer cells. The expression products of these genes can therefore be used as biomarkers for the diagnosis of the corresponding cancers. Examples of cancer markers include, but are not limited to, CA 125 (ovarian cancer), CA 15-3 and 27-29 (breast cancer), CA 19-9 (pancreas, colon, stomach cancer), carcinoembryonic antigen (ovarian, lung, breast, pancreas, and gastrointestinal tract cancers), alpha-fetoprotein (liver and testicular cancer), beta HCG (testicular cancer), calcitonin or thyroglobulin (thyroid cancer), and PSA (prostate cancer).

In still another embodiment, an analyte of interest is a component of a signal transduction pathway, or a binding partner thereof (e.g., inhibitors, stimulators, agonists, or antagonists). Non-limiting examples of signal transduction pathways that are amenable to the present invention include apoptosis pathways (such as caspase cascade, the p53 signaling pathway, ATM/p53 signaling pathway, or Fas signaling pathway), pathways involving cytokines, growth factors or hormones (such as EGF receptor signal transduction pathway, TNF signaling pathway, insulin pathway, or glucocorticoid receptor signaling), the JAK/STAT signaling pathway, STAT3 signaling pathway, PPAR signaling pathway, T cell receptor signaling, B cell receptor signaling, signaling by inositol phospholipids, ubiquitin-proteasome pathway, Akt signaling, mitogen-activated protein kinase cascades, oxidative stress pathway, lipid-mediated cell signaling, and noradrenergic, dopaminergic or serotonergic pathways.

The present invention features detection of unlabeled analytes in raw samples. As used herein, a raw sample refers to a sample which has not been subject to substantial purification. Such samples include, but are not limited to, blood, serum, saliva, sputum, tears, sweat, semen, urine, feces, cerebrospinal fluid, interstitial fluid, cellular extracts, tissue extracts, or other secreted, excremental or biologically-derived fluids or samples. Microbial samples, food/beverage samples, pharmaceutical samples, clinical samples, soil samples, or other naturally-occurring or artificially-produced samples that have complex compositions can also be analyzed according to the present invention. Moreover, analytes in partially purified samples can be detected according to the present invention. In many cases, the amount of the analyte being investigated in a raw sample is insignificant as compared to other organic components in the sample (e.g., by weight percentage or mole percentage). In one example, the analyte being investigated is a protein (or a nucleic acid) which constitutes less than 1%, 0.5%, 0.1%, or 0.01% by weight of the total protein content (or nucleic acid content) of the sample. In another example, the raw or partially purified sample comprises a significant amount of other proteins, nucleic acids, polysaccharides or lipids, which prevent the detection of the analyte of interest by conventional gel electrophoresis or chromatography (e.g., SDS-PAGE for protein, agarose gels for DNA/RNA, and thin layer chromatography for lipid or polysaccharide).

In yet another example, the raw sample is a lysate or supernatant of cultured cells, and the analyte being investigated is a recombinant protein expressed by the cultured cells. Host cells suitable for this purpose include eukaryotic cells (e.g., mammalian cells, insect cells or yeast) or prokaryotic cells (e.g., bacteria). Non-limiting examples of suitable eukaryotic host cells include Chinese hamster ovary cells (CHO), HeLa cells, COS cells, 293 cells, or CV-1 cells. Non-limiting examples of suitable prokaryotic host cells include *E. coli* (e.g., HB101, MC1061) or *B. subtilis*.

In one embodiment, the analyte being investigated is expressed as a cytoplasmic or membrane protein in the host cells. The lysate of the host cells is directly applied to an evanescent field sensing surface to detect interactions between the analyte and the capture molecules immobilized on the surface. In another embodiment, the analyte being investigated is expressed as a secreted protein, and the supernatant of the host cells is applied to the sensing surface to detect interactions between the secreted analyte and the immobilized capture molecules.

Any type of capture molecules can be immobilized to an evanescent field sensing surface. Non-limiting examples of such capture molecules include antibodies, antibody mimics, high affinity binders, antigens, peptides, proteins, lipids, polysaccharides, oligonucleotides, nucleic acids (e.g., cDNA, cRNA, mRNA), protein-binding ligands, receptors, small molecules, chemical compounds, cell fragments, cellular substructures, synapses, cell organelles, cancer cells, tissue samples, viruses, bacteria, or other microbes. Antibodies suitable for the present invention include, but are not limited to, polyclonal antibodies, monoclonal antibodies, chimeric antibodies, single chain antibodies, synthetic antibodies, Fab fragments, or fragments produced by Fab expression libraries. Methods for preparing antibodies that are specific to an analyte of interest are well known in the art. In many embodiments, the binding affinity of an immobilized capture molecule to the respective analyte is at least $10^4$ $M^{-1}$, $10^5$ $M^{-1}$, $10^6$ $M^{-1}$, $10^7$ $M^{-1}$, $10^8$ $M^{-1}$, or stronger.

Numerous methods are available for immobilizing capture molecules to an evanescent field sensing surface. In many embodiments, the capture molecules are attached to the sensing surface through an adhesion promoting layer. There are several ways in which this layer can be formed. One way is to silanize the sensing surface to form a layer of silane molecules and another way is to use a self-assembled monolayer (SAM). There are further methods available for immobilizing capture molecules, such as chemical modification of the sensing surface with reactive groups and the capture molecules with appropriate linkers (Maskos and Southern, NUCLEIC ACIDS RESEARCH, 20: 1679-84 (1992)), modification of the sensing surface and capture molecules with photoreactive linkers/groups (WO 98/27430 and WO 91/16425), immobilization via coulombic interaction (EP0472990 A2), or coupling via tags in chelating reactions.

In one example, the sensing surface is silanized with compounds such as 3-(glycidoxypropyl)trimethoxysilane, (3-aminopropyl)triethoxysilane, or mercaptomethyldi-methylethoxysilane. Proteins (e.g., antibodies) that contain multiple amino groups can react with the epoxy function of the silane. This allows covalent coupling of these proteins to a silanized surface. Nucleic acids or other capture molecules can be modified with amino groups, permitting immobilization of these molecules to a silanized surface.

In another example, the sensing surface is coated with avidin, and the capture molecules are conjugated with a biotin moiety. The high-affinity binding between biotin and avidin allows stable attachment of the capture molecules to the sensing surface.

An adhesion promoting layer can be further chemically modified to alter the surface properties. For example, a silanized surface can be reacted with functionalized saturated or unsaturated organic/hetero-organic/inorganic molecules or derivatives to manipulate hydrophobic/hydrophilic balance of the surface. In addition, ionic or potentially ionic compounds can be used to create positive or negative charges at the surface. In one example, 3-amino-1-propanol is used to modify the characteristics of a silanized surface. The nitrogen (amine group) introduced at the surface is quaternized by protons and, therefore, provides positive charges for interactions with negatively charged molecules, such as DNA, RNA or other types of nucleic acid molecules. In another example, polyethyleneglycol (PEG) or derivatives thereof are used to render the sensing surface hydrophilic, which can prevent non-specific absorption of proteins to the surface.

Reactive or photoreactive groups can also be attached to an evanescent field sensing surface. These groups can serve as anchor groups for stable coupling of capture molecules to the surface. In one example, a silanized sensing surface is coated with PEG derivatized with ethylenediamine groups. The ethylenediamine groups react with the thiol groups in oxidized proteins (e.g., antibodies), allowing covalent coupling of the proteins to the silanized surface.

A SAM can be obtained, for example, by treating the sensing surface with amphiphilic alkylphosphates (e.g. stearyl phosphate). The phosphate headgroup reacts with the hydroxy groups at the surface and leads to the formation of an ordered monolayer of the amphiphilic alkylphoshates. The hydrophophic alkyl chains render the surface hydrophobic and thus enable the physisorption of antibodies or other proteins. A SAM can also be used for immobilization of other capture molecules, e.g., DNA, RNA or PNA. In such a case, amphiphilic phosphates, or phosphates modified with amine or epoxy groups, can be used.

An adhesion promoting layer can also include multiple layers in order to produce desired surface characteristics, e.g. desired hydrophobicity, contact angle or charge density. The use of chemical linker molecules or photochemical linker molecules can also be considered as an intermediate adhesion promoting layer. This controlled combination of layers or molecules with different functionalities can create a supramolecular structure which provides a functionality that differs from that of individual molecules.

In addition, adhesion promotion can be achieved by deposition of microporous layers or gels on the evanescent field sensing surfaces. The use of microporous layers or gels can enhance the surface attachment of the capture molecules. It can also improve the detection sensitivity for the analytes of interest. Materials suitable for making microporous layers include, but are not limited to, polymers, glass, quartz, ceramic, or fused silica.

The concentration of the capture molecules that are immobilized to a sensing surface can be in any desired range, such as from about 1 to about 10 molecule/$cm^2$, from about 10 to about $10^2$ molecule/$cm^2$, from about $10^2$ to about $10^3$ molecule/$cm^2$, from about $10^3$ to about $10^4$ molecule/$cm^2$, from about $10^4$ to about $10^5$ molecule/$cm^2$, from about $10^5$ to about $10^6$ molecule/$cm^2$, from about $10^6$ to about $10^7$ molecule/$cm^2$, or more. The capture molecules can be randomly distributed in the sensing surface, or organized in a predefined pattern (such as a regularly spaced array). Each sensing surface may include only one type of capture molecules. It can also include two or more different types of capture molecules.

The present invention features the use of evanescent field sensing to detect unlabeled analytes in raw or partially purified samples. A raw or partially purified sample can be directly applied to an evanescent field sensing surface. The interaction between an analyte in the sample and the immobilized capture molecules alters the refractive index at the surface, which in turn produces a shift in the resonant wavelength or resonant angle. These resonant conditions can be interrogated by observing the reflected light in order to determine the corresponding refractive index changes. Many methods are available for this purpose. For instance, where a grating-coupled waveguide is used, the refractive index changes can be monitored by either spectral interrogation or angular interrogation. In spectral interrogation, a nominally collimated, broadband light beam is sent into the grating-coupled waveguide and the reflected light is collected and monitored with a spectrometer. By observing the spectral location of the resonant wavelength (peak), one can monitor binding or refractive index changes on or near the evanescent field sensing surface. In angular interrogation, a nominally single wavelength is focused to create a range of illumination angles and directed into the grating-coupled waveguide. The reflected light can be monitored with a CCD camera or other optical detectors. By monitoring the position of the resonant angle reflected by the grating-coupled waveguide, one can also monitor binding or refractive index changes on or near the evanescent field sensing surface.

In many embodiments, the evanescent field sensing allows detection of an unlabeled, unpurified analyte at a concentration of less than $10^{-7}$ M. In certain instances, the evanescent field sensing enables detection of an unlabeled, unpurified analyte at a concentration of less than $10^{-8}$ M, such as less than $10^{-9}$ M, $10^{-9}$ M, $10^{-10}$ M, $10^{-11}$ M, or $10^{-12}$ M.

The desired signal for an analyte of interest can be enhanced by removing non-specific signals. This can be achieved by disrupting or reducing weak or non-specific interactions with the sensing surface. Any method known in the art can be used for this purpose, such as by adding detergents, salts, or other additives. The sensing surface can also be pre-treated to block non-specific binding sites. In addition, control samples can be used. The refractive index changes observed in these control samples can be used as the baseline changes and subtracted from the refractive index changes observed in the sample of interest, thereby eliminating or reducing the contributions from non-specific bindings.

Evanescent field sensing with raw or partially purified samples can be used in a wide array of applications. Non-limiting examples of such applications include diagnostics (e.g., detection of pathogenic agents, or antibodies thereto, in blood or other bodily fluids), bioterror detection or prevention (e.g., detection of anthrax or smallpox in food or environmental samples), cancer screening (e.g., detection of cancer markers in tissue samples), molecular interaction (e.g., detection of protein-protein, protein-nucleic acid, protein-lipid, protein-carbohydrate, protein-small molecule, nucleic acid-nucleic acid, nucleic acid-small molecule, or lipid-small molecule interactions), high throughput screening (e.g., identification of modulators for kinases, phosphatases, ion channels, G protein coupled receptors, proteases or other drug targets), toxicoproteomics, gene expression, analysis of splicing variants, analysis of single nucleotide polymorphism, or determination of kinetic parameters for binding activities (e.g., affinity constants). These applications typically involve applying a raw sample to an evanescent field sensing surface and monitoring the refractive index changes at the surface to determine interactions between an analyte in the sample and the immobilized capture molecules. Other applications that involve detection or evaluation of molecular interactions can also be performed according to the present invention.

The detection of an unpurified, unlabelled analyte can be either qualitative or quantitative. For quantitative analysis, samples comprising known concentrations of an analyte of interest can be used as references to determine the concentration-dependent refractive index changes at the sensing surface. The concentration of the analyte of interest in a test sample can then be determined by comparing to the reference samples.

It should be understood that the above-described embodiments and the following example are given by way of illustration, not limitation. Various changes and modifications within the scope of the present invention will become apparent to those skilled in the art from the present description.

EXAMPLE

A label-independent detection (LID) system developed by Corning Inc. was used to evaluate interactions between unlabeled streptavidin and immobilized biotin. This LID system is comprised of a multi-well optical reader and a disposable microplate (e.g., a 96- or 384-well microplate). Each well of the microplate contains a grating-coupled waveguide for evanescent field sensing. The sensing surface has a surface chemistry layer allowing for attachment of molecules that contain primary amine groups (e.g., biotin-amine). As streptavidin or other analytes of interest bind to the sensing surface, the refractive index at the surface is changed. An optical mode propagates and senses the refractive index changes close to the sensing surface. Only light that is "resonant" is strongly reflected, and the exact wavelength of the resonance is a sensitive function of the refractive index at the surface of the sensor.

In a typical operation, a baseline read of the microplate is first established. Addition of a binding partner results in a change in refractive index at the sensing surface, which is indicated as picometer (pm) shift from baseline. Each microplate is read on the optical reader before, during, and after the addition of the binding partner. Resonant wavelength shift ("Response (pm)") is plotted as a function of time.

Cell lysate was prepared by diluting a 2 mg/ml stock to 100 µg/ml final concentration. A Corning 96-well clear polystyrene non-treated flat bottom plate (Corning catalog # 3370) was used for source plate preparation. To facilitate efficient pickup of the sample solutions by a multi-channel robotic pipettor in the LID instrument, each well of the source plate contained extra solution. A solution of 1× phosphate buffered saline (PBS; 1 mM $KH_2PO4$, 10 mM $Na_2HPO4$, 137 mM NaCl, and 2.7 mM KCl) was used as a first addition step for baseline measure. A solution of 200 nM (12 µg/ml) streptavidin (Sigma catalog # S-4762) in 1× PBS was used in streptavidin-only source wells. An identical concentration was prepared in cell lysate to render an equivalent final concentration in the source plate.

The source plate was set up as follows: PBS was added to wells A-H on columns 1 and 2 on the source plate (FIG. 1). Cell lysate containing streptavidin (STR+lys) was added to wells A, B, and C in columns 7 and 8 of the source plate. Lysate alone (lys) was added to wells C, D and G in columns 7 and 8. Streptavidin alone (STR) was added to wells E and H in columns 7 and 8.

Samples on the source plate were selected and transferred to the LID microplate for interrogation. The microplate was set up as follows: Biotin-amine was prepared using a solution of 10 µM (3.7 µg/ml) biotin-amine (Pierce catalog # 21346) in 150 mM borate buffer (pH 9.2). A solution of 200 mM ethanolamine (EA) in 150 mM borate buffer (pH 9.2) was also prepared. Immobilization was performed with addition of 75 µl biotin-amine solution ("BIOTIN") or 75 µl ethanolamine solution ("EA") to the corresponding wells, followed by incubation at room temperature for 30 minutes (FIG. 1).

Interactions between purified streptavidin and immobilized biotin were first evaluated (FIG. 2). Biotin was immobilized to the microplate as a target. PBS was added to establish a baseline read (before point A). Purified streptavidin was then added, producing an increase in the bulk index (indicated as picometer shift from baseline, i.e., "Response (pm)") due to binding to the immobilized biotin (between points A and B). Ethanolamine in borate buffer (pH 9) was added, resulting in a bulk index shift (after point B) which was removed after washing with PBS buffer (after point C). Response curves A-E were replicates of purified streptavidin being added to immobilized biotin; response curves F-G were purified streptavidin being added to immobilized dextran (negative target control); and response curve H was purified streptavidin being added to immobilized ethanolamine (another negative target control).

Figure 3:
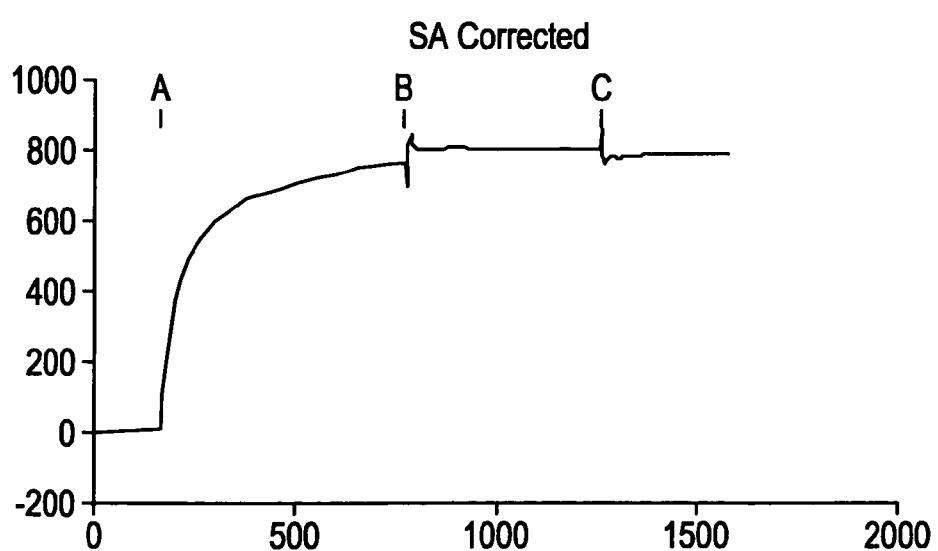
FIG. 3 is a corrected LID response curve indicating the bulk index shift due to interactions between purified streptavidin and immobilized biotin.

FIG. 3 depicts a corrected LID response curve indicating the bulk index shift due to the binding between purified streptavidin and immobilized biotin. Response curves F-H in FIG. 2 were averaged and then subtracted from the average of response curves A-E. The resulting curve (FIG.

3) indicates the bulk index shift due to streptavidin binding to biotin (after point A). Ethanolamine in borate buffer (between points B and C) did not appear to bind to the target area, and post wash (after point C) did not disrupt the binding of streptavidin to biotin.

Figure 4:
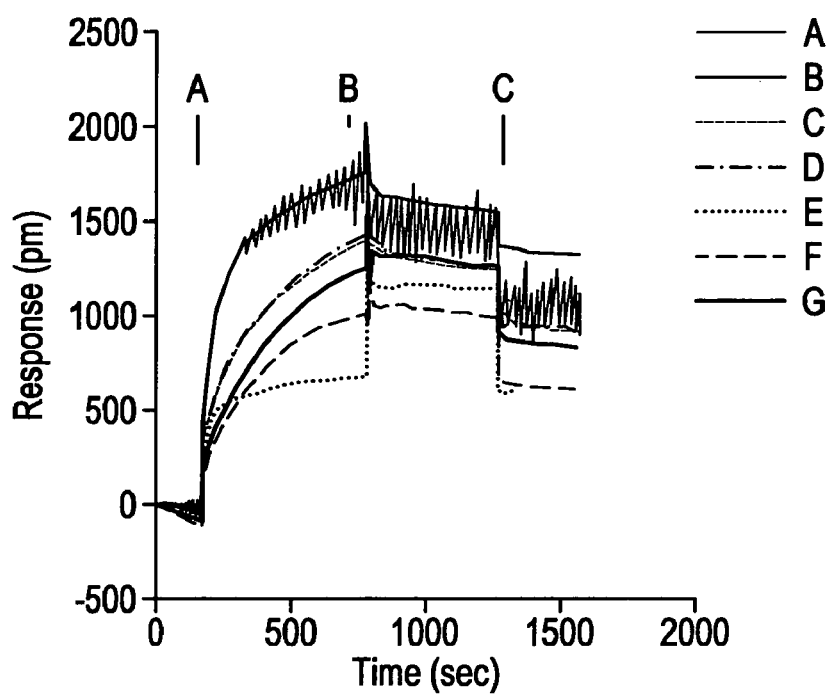
FIG. 4 demonstrates LID interrogation of interactions between streptavidin in cell lysate and immobilized biotin.

FIG. 4 shows the testing results using unpurified streptavidin and immobilized biotin. HeLa whole-cell lysate containing the same concentration of streptavidin as shown in FIG. 2 was added to the LID microplate. Response curves A-B were replicates of cell lysate with streptavidin being added to immobilized biotin; response curves C-D were replicates of cell lysate without streptavidin being added to immobilized biotin (to determine influence of lysate on signal response); response E was purified streptavidin being added to immobilized biotin (as positive control); response curve F was lysate with streptavidin on dextran (negative control to determine non-specific binding); and response curve G was lysate without streptavidin on dextran (another negative control to determine non-specific binding). Like in FIG. 2, PBS was added to establish a baseline read (before point A in FIG. 4). Cell lysate samples or controls were added, producing shifts in the bulk index due to interactions with immobilized biotin (between points A and B in FIG. 4). Ethanolamine in borate buffer (pH 9) was then added (after point B) and removed by washing with PBS buffer (after point C).

Figure 5:
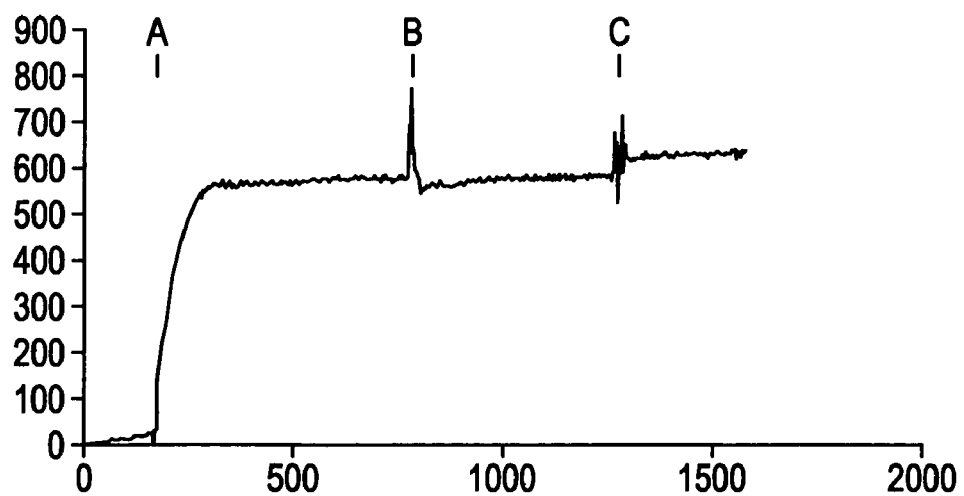
FIG. 5 is a corrected LID response curve indicating the bulk index shift due to interactions between streptavidin in cell lysate and immobilized biotin.

Response curves A and H in FIG. 4 were discarded as noisy channels. Averaging the values from response curves C-D and removing this value from response curve B and then correcting for the average of F-G resulted in the corrected response for streptavidin binding to biotin as shown in FIG. 5

The foregoing description of the present invention provides illustration and description, but is not intended to be exhaustive or to limit the invention to the precise one disclosed. Modifications and variations consistent with the above teachings may be acquired from practice of the invention. Thus, it is noted that the scope of the invention is defined by the claims and their equivalents.

What is claimed is:

1. A method for evaluating interactions between an analyte of interest and a capture molecule, said method comprising:
   contacting a liquid raw sample with a sensing surface of an evanescent field sensor, wherein the liquid raw sample comprises the analyte of interest, and the sensing surface is coated with the capture molecule; and
   detecting a change in refractive index at the sensing surface, wherein the change in the refractive index indicates whether the analyte of interest interacts with the capture molecule,
   wherein the liquid raw sample is selected from the group consisting of a lysate, a supernatant of cultured cells, a bodily fluid, and a tissue extract, and the analyte is selected from the group consisting of a recombinant protein expressed by the cultured cells, a pathogen marker, an antibody specific to the pathogen marker, and a cancer cell marker.

2. The method of claim 1, wherein the evanescent field sensor comprises at least one grating-coupled waveguide.

3. The method of claim 2, wherein detecting a change in refractive index comprises:
   contacting a liquid control sample with the sensing surface;
   detecting a baseline change in refractive index at the sensing surface; and
   comparing the refractive index change produced by the liquid raw sample to the baseline change, wherein the liquid control sample is a lysate or supernatant of culture cells that do not express the recombinant protein.

4. The method of claim 2, wherein detecting a change in refractive index comprises:
   directing a light beam into said grating-coupled waveguide, wherein the light beam diffracts to produce an evanescent tail that extends beyond the sensing surface;
   receiving a reflected light beam from the grating-coupled waveguide; and
   detecting a resonant condition that indicates whether the analyte of interest is bound to the capture molecule.

5. The method of claim 2, wherein said grating-coupled waveguide comprises:
   a substrate having a refractive index of no more than 1.5,
   a diffraction grating, and
   a waveguide film comprising said sensing surface, wherein said waveguide film has a higher refractive index than the substrate.

6. A method for evaluating molecular interactions, comprising:
   contacting a plurality of liquid raw samples with respective sensing surfaces of an evanescent field sensor, wherein each liquid raw sample comprises an analyte of interest, and each sensing surface is coated with a capture molecule; and
   detecting a change in refractive index at each sensing surface, wherein the change in the refractive index at each sensing surface after being contacted with each liquid raw sample is indicative of whether the analyte of interest in that liquid raw sample interacts with the capture molecule coated at each sensing surface, wherein the liquid raw sample is selected from the group consisting of a lysate, a supernatant of cultured cells, a body fluid sample, and a tissue extract, and the analyte is selected from the group consisting of a recombinant protein expressed by the cultured cells, a pathogen marker, an antibody specific to the pathogen marker, and a cancer cell marker.

7. The method of claim 6, wherein the evanescent field sensor comprises a microplate which includes a plurality of wells, each well comprising a grating-coupled waveguide that includes at least one sensing surface.

8. The method of claim 7, wherein the grating-coupled waveguide in each said well comprises:
   a substrate having a refractive index of no more than 1.5;
   a diffraction grating; and
   a waveguide film comprising one said sensing surface, wherein said waveguide film has a higher refractive index than the substrate.

9. A method for detecting the presence or absence of an analyte of interest in a liquid raw sample, said method comprising:
   contacting said raw sample with a sensing surface of an evanescent field sensor, the sensing surface being coated with capture molecules capable of binding to the analyte of interest; and
   detecting a change in refractive index at the sensing surface, wherein the change in the refractive index after the contacting is indicative of the presence or absence of the analyte of interest in the liquid raw sample, wherein the liquid raw sample is selected from the group consisting of a lysate, a supernatant of cultured cells, a body fluid sample, a food sample, a beverage sample, an environmental sample, and a tissue extract, and the analyte is selected from the group consisting of a recombinant protein expressed by the cultured cells, a toxin, a pathogen, a pathogen marker, an antibody specific to the pathogen marker, and a cancer cell marker.

10. The method of claim 9, wherein the evanescent field sensor comprises at least one grating-coupled waveguide.

11. The method of claim 10, wherein said grating-coupled waveguide comprises:
a substrate having a refractive index of no more than 1.5,
a diffraction grating, and
a waveguide film comprising said sensing surface,
wherein said waveguide film has a higher refractive index than the substrate.

12. The method of claim 9, wherein the antibody is an antibody specific to an epitope of a pathogen, and the capture molecules comprise the epitope.

13. The method of claim 12, wherein said pathogen is a virus or a bacterium.

14. The method of claim 9, wherein the analyte is a cancer cell marker, and the capture molecules are antibodies specific to the cancer cell marker.

15. The method of claim 9, wherein detecting a change in refractive index comprises:
directing a light beam into the grating-coupled waveguide, wherein the light beam diffracts to produce an evanescent tail that extends beyond the sensing surface;
receiving a reflected light beam from said grating-coupled waveguide; and
detecting a resonant condition that indicates whether the analyte of interest is bound to the capture molecules.

16. A method for identifying binding partners of a target molecule, the method comprising:
contacting a liquid raw sample with a sensing surface of an evanescent field sensor, wherein the sensing surface is coated with the target molecule, and the liquid raw sample includes a molecule of interest; and
detecting a change in refractive index at the sensing surface, wherein the change in the refractive index in the presence of the liquid raw sample, as compared to that in the presence of a liquid control sample that does not include the molecule of interest, is indicative of whether the target molecule is capable of interacting with the molecule of interest, wherein the liquid raw sample is selected from the group consisting of a lysate, a supernatant of cultured cells, a body fluid sample, and a tissue extract, and the analyte is selected from the group consisting of a recombinant protein expressed by the cultured cells,
a pathogen marker,
an antibody specific to the pathogen marker, and
a cancer cell marker.

17. The method of claim 16, wherein the evanescent field sensor includes one or more grating-coupled waveguides, each said grating-coupled waveguide comprising:
a substrate;
a diffraction grating; and
a waveguide film that comprises an evanescent field sensing surface.

18. The method of claim 17, wherein the substrate has a refractive index of no more than 1.5, and the waveguide film has a higher refractive index than the substrate.

* * * * *